(12) United States Patent
Whittlinger

(10) Patent No.: US 8,053,230 B2
(45) Date of Patent: Nov. 8, 2011

(54) CULTURE DISH WITH LID

(75) Inventor: Keith Owen Whittlinger, Penfield, NY (US)

(73) Assignee: Nalge Nunc International Corporation, Rochester, NY (US)

(*) Notice: Subject to any disclaimer, the term of this patent is extended or adjusted under 35 U.S.C. 154(b) by 430 days.

(21) Appl. No.: 11/846,193

(22) Filed: Aug. 28, 2007

(65) Prior Publication Data

US 2008/0064090 A1    Mar. 13, 2008

Related U.S. Application Data

(60) Provisional application No. 60/842,733, filed on Sep. 7, 2006.

(51) Int. Cl.
C12M 1/22    (2006.01)

(52) U.S. Cl. .................. 435/305.2; 435/305.3; 422/536; 422/559

(58) Field of Classification Search .... 435/305.1–305.4; 422/503, 536, 552, 559, 569
See application file for complete search history.

(56) References Cited

U.S. PATENT DOCUMENTS

| | | |
|---|---|---|
| 3,097,070 A | 7/1963 | Aldrich et al. |
| 4,042,463 A | 8/1977 | Haque et al. |
| 4,452,679 A | 6/1984 | Dunn et al. |
| 4,665,035 A | 5/1987 | Tunac |
| 4,919,659 A | 4/1990 | Horbett et al. |
| 4,927,676 A | 5/1990 | Williams et al. |
| 5,051,312 A | 9/1991 | Allmer |
| 5,151,366 A | 9/1992 | Serkes et al. |
| 5,308,704 A | 5/1994 | Suzuki et al. |
| 5,449,383 A | 9/1995 | Chatelier et al. |
| 5,578,490 A * | 11/1996 | Martinez Ubeira ........ 435/287.1 |
| 5,856,176 A * | 1/1999 | Mathus et al. ............. 435/288.3 |
| 6,448,069 B1 | 9/2002 | Cecchi et al. |
| 6,617,152 B2 | 9/2003 | Bryhan et al. |
| 6,905,105 B2 | 6/2005 | Boyce |
| 2002/0192811 A1* | 12/2002 | Pitt et al. .................... 435/297.5 |
| 2007/0128081 A1 | 6/2007 | Ellis et al. |
| 2008/0003672 A1* | 1/2008 | Cecchi et al. ............. 435/305.2 |

FOREIGN PATENT DOCUMENTS

| | | |
|---|---|---|
| DE | 1 267 445 | 5/1968 |
| GB | 2 187 474 | 8/1987 |
| GB | 2 262 538 | 6/1993 |
| WO | 9736992 | 10/1997 |

OTHER PUBLICATIONS

Barnaby Hoyal, International Search Report and Written Opinion, Jan. 3, 2008, 10 pages, European Patent Office.

(Continued)

*Primary Examiner* — William H Beisner
*Assistant Examiner* — Michael Hobbs
(74) *Attorney, Agent, or Firm* — Wood, Herron & Evans, LLP

(57) ABSTRACT

A device for culturing cells or tissue includes a culture dish with a bottom wall and at least one sidewall to define an interior cavity, at least one channel formed on the bottom wall to minimize the effect of fluid movement on biologics in the dish and, optionally, at least one barrier wall for partitioning the interior cavity into a plurality of compartments. The barrier wall maintains a biologic in one compartment separate from a biologic in another compartment. The barrier wall may also provide fluid communication between compartments.

16 Claims, 5 Drawing Sheets

OTHER PUBLICATIONS

Corning Incorporated; Corning Square BioAssay Dishes-Beyond the Standard; 2 pages.
Nalge Nunc International; Nunc Low Profile Bioassay Dish; copyright 2003; 4 pages.
Ortec International; OrCel; copyright 2002; 2 pages.
Barnaby Hoyal; Examination Report issued in related European Patent Application No. 07 841 969.4; Mar. 26, 2010; 4 pages; European Patent Office.
Jambor Eszter; Written Opinion issued in related Singapore Patent Application No. 2009014135; Mar. 12, 2010; 10 pages; Hungarian Patent Office.
Chinese Patent Office, First Office Action, in related Chinese Application No. 200780032837.2, dated Mar. 2, 2011.
Intellectual Property Office of Singapore, Examination Report, in related Sinagporean Application No. 200901413-5, dtd Jan. 21, 2011.

* cited by examiner

CULTURE DISH WITH LID

CROSS-REFERENCE TO RELATED APPLICATIONS

This application claims priority to U.S. Provisional Application Ser. No. 60/842,733 filed Sep. 7, 2006, the disclosure of which is incorporated by reference herein in its entirety.

TECHNICAL FIELD

Cell and tissue culture devices.

BACKGROUND

Tissue engineering is increasingly useful as a therapeutic tool, particularly for treating skin wounds or vascular disease, and also as a tool for testing certain pharmaceuticals and cosmetics. For example, numerous skin substitute products are commercially available. Most of these products comprise a porous matrix of some type, often infiltrated with fibroblasts at the time of use, to function as a dermal layer and having keratinocytes or a thin epidermal autograft as an epidermal layer.

One such product is OrCel® (Ortec International, Inc.), a bilayer skin replacement having a collagen sponge that, upon use, contains allogenic dermal fibroblasts cultured on and within it as a dermal layer, and cultured allogenic keratinocytes on a non-porous side of the collagen sponge as an epidermal layer. Another bilayer skin replacement product, PermaDerm® (Cutanogen Corporation/Lonza, Walkersville, Inc.; Walkersville Md.), uses epidermal and dermal cells, preferably of autologous source, cultured on and within a collagen matrix. These exemplary products illustrate the vital role of cell culture in the preparation of such skin replacement products for therapeutic and/or research use.

Cell culture inserts comprising porous membranes, such as those sold by Nunc A/S (Roskilde, Denmark), are useful for studies of epithelial polarization, chemotaxis, macromolecule transport, and other applications. Generally, a porous membrane of either inorganic material, such as Anopore® (Anotec Separations Ltd.), or organic material, such as polycarbonate, serves as the growth and/or attachment surface for cultured cells, while the membrane is fixed to a rigid frame of culture-compatible material, such as polystyrene, that holds the membrane away from the bottom of the culture dish to allow culture media to reach both sides of the cells attached to and/or growing on the membrane.

To date, sponges, fabrics, membranes and other types of porous matrices for containing and supporting living cells, typically have been cultured in standard culture dishes, including those commonly referred to as bioassay dishes. Examples of bioassay dishes include Nunc® bioassay dishes, such as product numbers 240835 and 240845, and Corning® bioassay dishes, such as product numbers 431111 and 431301 (Corning Life Sciences, Acton Mass.). Bioassay dishes were initially designed for use with microbes, such as bacteria and yeasts, or non-anchorage dependent eukaryotic cells and are generally rigid transparent plastic dishes with a large surface area but having a low height so that multiple dishes may be stacked in an incubator.

Standard bioassay dishes have several drawbacks. Because skin replacement products require relatively large amounts of nutritive medium to progressively feed the growing structure, addition of medium is typically necessary. However, it is difficult to add culture medium to a standard bioassay dish without disrupting, displacing or otherwise damaging the cells in the dish. Moreover, the large volumes of media that must be contained in such dishes leads to excessive medium movement or sloshing when a bioassay dish must be moved or otherwise handled; this is undesirable due to the low profile or height of bioassay dishes.

There is thus a need for alternative culture dishes.

SUMMARY

A culture dish capable of containing one or more biologics (e.g., matrices) for supporting the infiltration of living cells, having a channel wherein culture medium or other components may be added thereto without disrupting or damaging the cells and the liquid contents of the dish have a reduced susceptibility to excessive movement or sloshing during manipulation and handling of the dish. One skilled in the art will appreciate that cell culture includes tissue culture because tissues are a higher organization of cells. A culture dish, also referred to as a bioassay dish, includes a bottom wall and at least one sidewall projecting upwardly from the bottom wall to define an interior cavity. In one embodiment, the culture dish further includes at least one barrier wall for partitioning the interior cavity into a plurality of compartments, wherein the barrier wall is configured to maintain a first biologic in a first compartment physically separate from a second biologic in a second compartment. The barrier wall may include at least one opening for providing fluid communication between the first and second compartments. In one embodiment, the barrier wall includes a plurality of discrete barrier blocks that define openings between adjacent barrier blocks for fluid communication.

In one embodiment, a lid may be removably coupled to the culture dish to at least partially cover the interior dish cavity. The lid may include a top wall and at least one sidewall projecting downwardly from the top wall. The culture dish and/or the lid may include at least one spacer for providing at least a portion of a flow path from outside the culture dish to the interior cavity of the culture dish when the lid is placed thereon. For example, in one embodiment, the spacers may include projections (e.g., vent lugs) that space the top wall of the lid from the culture dish. In another embodiment, the spacers may be projections (e.g., ribs) that space the sidewalls of the lid from the culture dish.

In other embodiments, the culture dish and/or lid may include additional features. For example, the culture dish and lid may include projections that limit lateral sliding of one device relative to an adjacent device when the devices are in a stacked configuration. The device may include an orientation indicator for orienting the lid relative to the culture dish. Furthermore, the culture dish may include indicia for identifying the different compartments.

In another embodiment, a device for culturing cells or tissue includes a culture dish having a bottom wall and at least one sidewall projecting upwardly therefrom to define an interior cavity, and at least one channel in the bottom wall for adding and/or removing fluid to/from the culture dish in a manner that minimizes the effects on a biologic located in the culture dish. In one embodiment, the channel may be formed from a pair of generally parallel, spaced ridges and extend, for example, across the entire dimension of the culture dish. The dish may further include at least one barrier wall for partitioning the interior cavity of the culture dish into a plurality of compartments. In one embodiment, the barrier wall may include a plurality of barrier blocks wherein at least one of the barrier blocks includes a portion that forms part of the channel. The channel may be configured to be in fluid communication with each of the compartments in the culture dish.

The above and other objects and advantages of the invention shall be made apparent from the accompanying drawings and the description thereof.

BRIEF DESCRIPTION OF THE DRAWINGS

The accompanying drawings, which are incorporated in and constitute a part of this specification, illustrate embodiments together with the general description above and the detailed description of the embodiments below.

DETAILED DESCRIPTION

Figure 1:
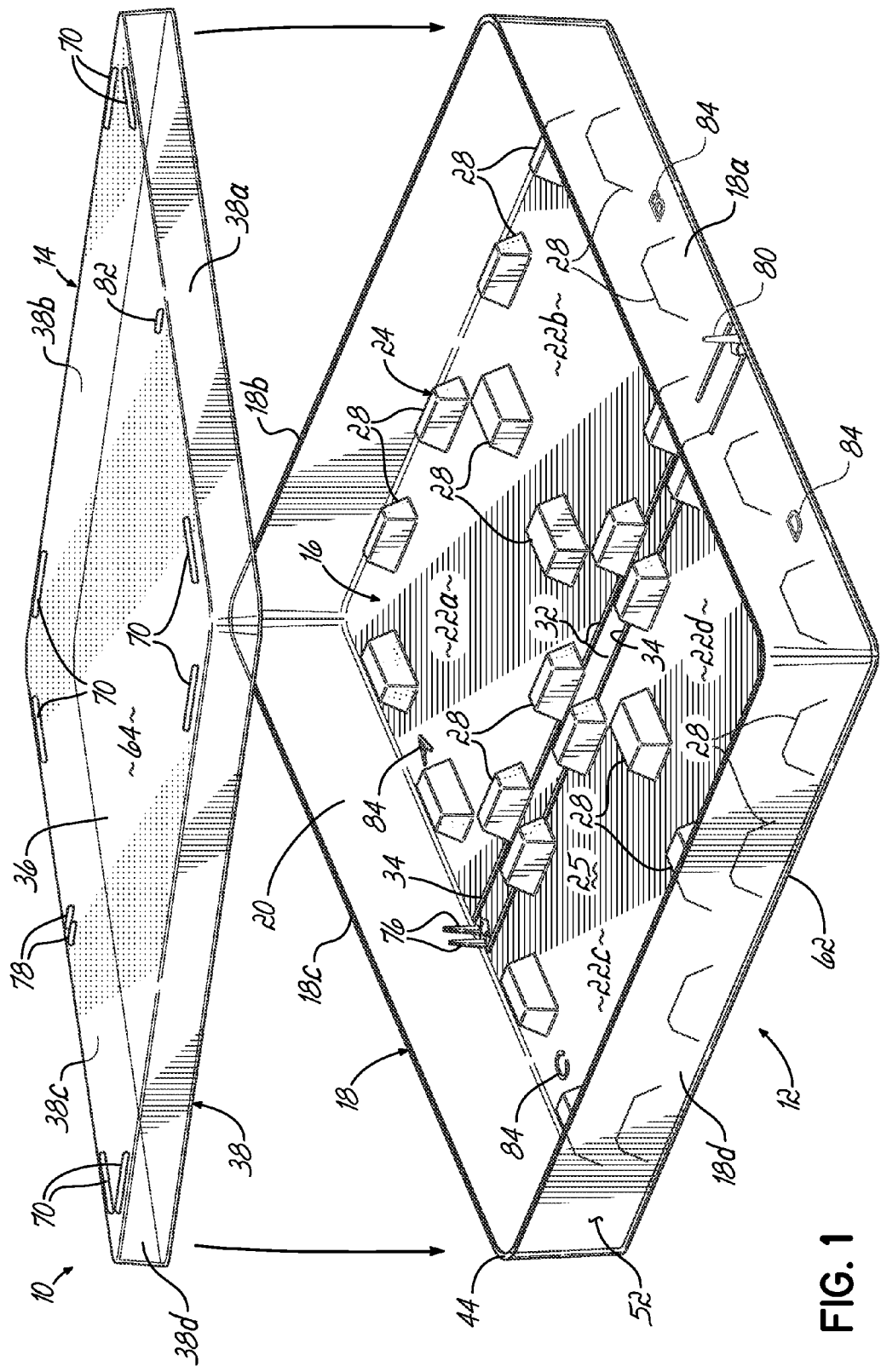
FIG. 1 is a disassembled perspective view of a culture dish assembly in accordance with one embodiment.
Figure 2:
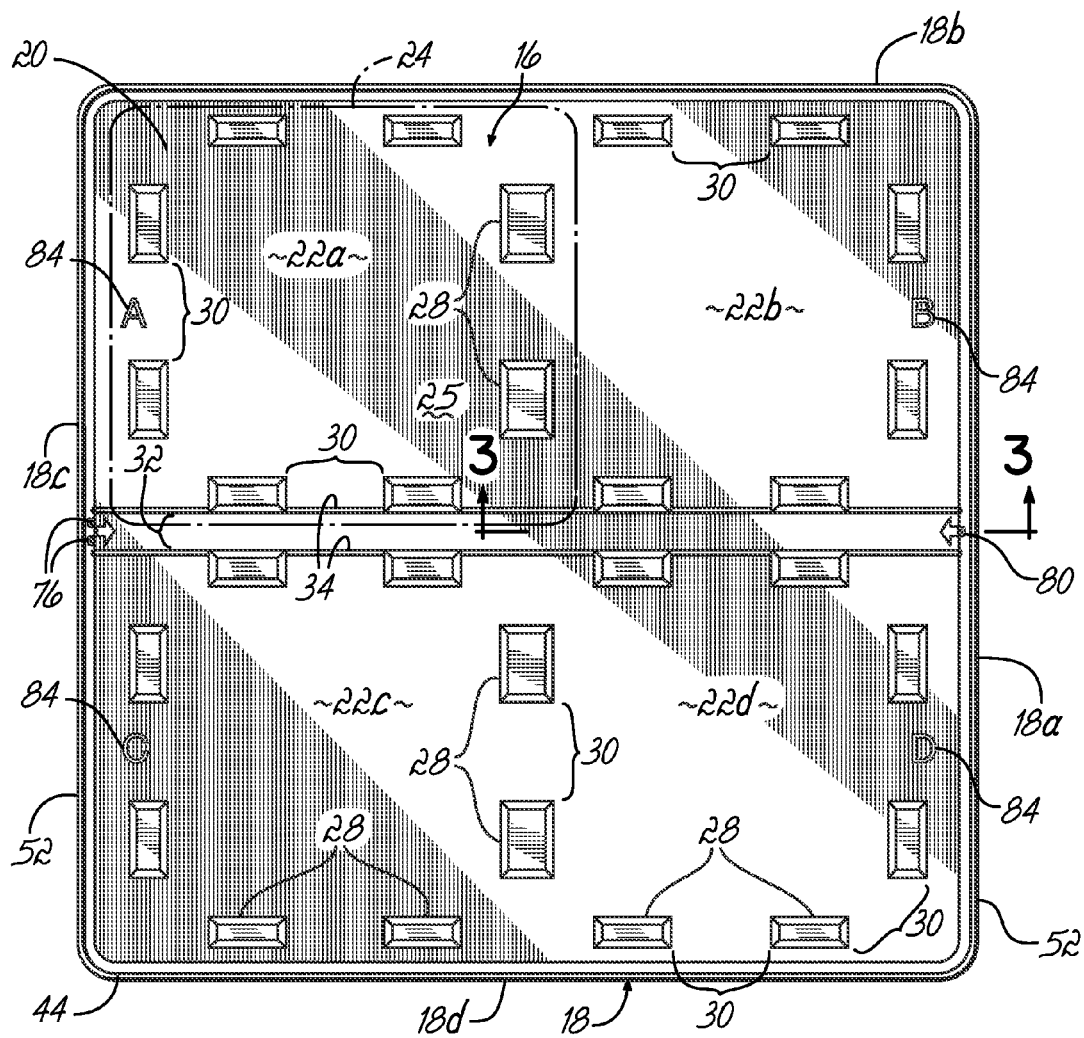
FIG. 2 is a top plan view of the culture dish shown in FIG. 1.
Figure 3:
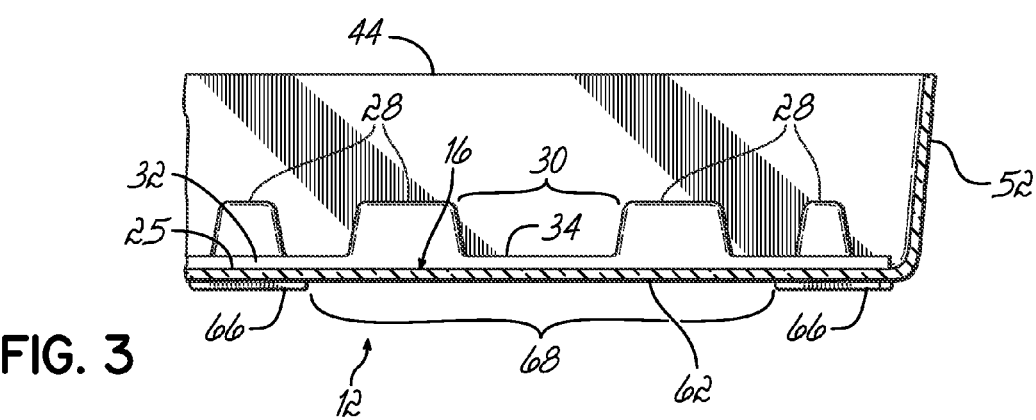
FIG. 3 is a partial cross-sectional view of the culture dish taken generally along line 3-3 in FIG. 2.

In reference to the drawings, FIG. 1 illustrates one embodiment of a device referred to herein as a culture dish assembly 10. The culture dish assembly 10 includes a culture dish 12 and a lid 14 adapted to be used therewith for culturing biologics (e.g., cells, tissue, etc.) for use in a wide range of medical applications. As shown in FIGS. 1-3, the culture dish 12 includes a substantially flat bottom wall 16 and one or more sidewall 18 projecting upwardly from an edge thereof to define an interior cavity 20. As illustrated in the figures, in one embodiment, the culture dish 12 may be generally square having sidewalls 18a-18d that, in combination with bottom wall 16, form interior cavity 20. Embodiments are not limited to the square configuration shown, but may be configured in a wide range of shapes and sizes. For example, the culture dish 12 may be generally rectangular, circular, oval, triangular, pentagonal, etc.

In one embodiment, the interior cavity 20 of the culture dish 12 may be partitioned for maintaining multiple biologics (e.g., matrices or inserts) physically separated from one another so that they do not contact each other, overlap each other, or otherwise effect the culturing of one biologic due to the presence of the other biologic. In one embodiment, the interior cavity 20 of culture dish 12 may define a plurality of compartments (e.g., compartments 22a-22d) therein, each compartment being adapted to receive one such biologic (not shown) therein. By way of example, as shown in FIG. 2, the culture dish 12 may include four such compartments 22a-22d, but the number of compartments may be varied depending on the specific application, user preference, and other factors. For example, the width and length of the culture dish 12, and/or the dimensions of the compartments may be varied to accommodate a desired number of compartments and/or the size of the biologics being used therewith.

In one embodiment, the compartments 22a-22d may be bounded by a barrier wall 24 that projects from an inside surface 25 of bottom wall 16 that defines an interior space for receiving the biologics. The barrier wall 24 bounds at least a portion of the interior space to prevent undesired movement of the biologic therein. As noted above, such an arrangement maintains multiple biologics in culture dish 12 physically separate from one another. In addition to maintaining multiple biologics separate from one another, it may also be desirable to provide fluid communication between the compartments 22a-22d in culture dish 12. Such fluid communication may provide uniform circulation and exposure to the culture medium in the culture dish 12. Thus, in one embodiment, the barrier wall 24 may include a plurality of raised barrier blocks 28 along the periphery of each of the compartments 22a-22d. The raised barrier blocks 28 are sufficient to maintain the biologics physically separate from each other in culture dish 12, and further define openings or gaps 30 between adjacent barrier blocks 28 to provide fluid communication between a first compartment (e.g., 22a) and a second compartment (e.g., 22b). In one embodiment, each compartment 22a-22d may be in fluid communication with each of the other compartments.

While the barrier wall 24 is shown in one embodiment as discrete barrier blocks 28 separated by openings 30, the barrier wall 24 may alternatively include substantially continuous walls with one or more openings for providing fluid communication between compartments (not shown). For example, the barrier wall 24 may be a substantially solid wall with one or more aperture, slit, fenestration, etc. extending therethrough to provide fluid communication between adjacent compartments. While the barrier wall 24 for defining the interior space of the compartments 22a-22d is shown as generally square, other shapes are also possible including, without limitation, generally rectangular, circular, oval, triangular, pentagonal, or other desirable shapes.

In addition to partitioning the interior cavity 20, the culture dish 12 may further include a channel 32 for adding and/or removing medium or other fluids (e.g., wash fluids) to/from culture dish 12 in a manner that reduces undesirable effects on the biologics positioned therein. In this embodiment, the channel 32 may be defined by a pair of generally parallel, spaced ridges 34 that project from the inside surface 25 of bottom wall 16 and extend therealong. For example, the ridges 34 may extend the entire dimension (e.g., length, width, diameter, etc.) of the culture dish 12, though not so limited. In one embodiment, the culture dish 12 may include a single channel 32 located substantially in the center of the culture dish 12. Other configurations are also within the scope of the culture dish 12. By way of example, the culture dish 12 may include multiple channels 32 (not shown), or a single channel 32 may be positioned off-center and located closer to an edge of the culture dish 12 (not shown). As those of ordinary skill in the art will recognize, the number and location of the channel(s) 32 may be varied as needed in the specific application.

In one embodiment, the channel 32 may be formed between adjacent pairs of compartments (FIG. 2). In such an embodiment, the barrier wall 24 that defines at least a portion of the compartments may be integrally formed with the ridges 34 that form channel 32 such that a portion of the barrier wall 24 forms a portion of the channel 32. For example, as shown in FIG. 3, at least a portion of one or more barrier blocks 28 form a portion of the channel 32. Alternatively, the barrier wall 24 may be formed separate from the ridges 34 (not shown).

Figure 4:
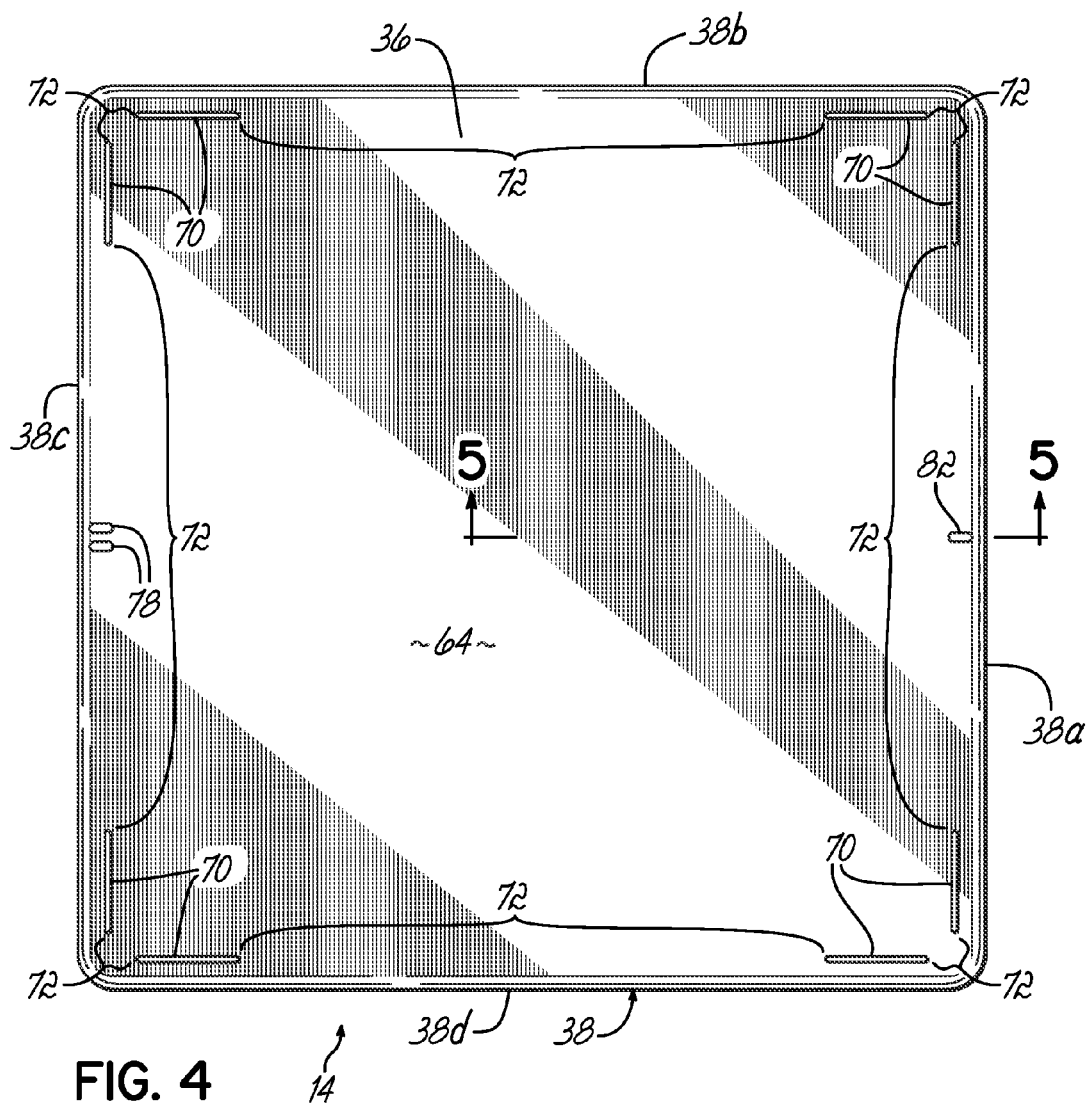
FIG. 4 is a top plan view of the lid shown in FIG. 1.

The physical dimensions of portions of the culture dish 12 may vary depending on, for example, the specific application, user desires, types of biologics, and other factors. Nevertheless, in one embodiment, such as illustrated in FIGS. 1, 2 and 4, the culture dish 12 may be configured as a square having sides of about 8.75 inches. The height of the ridges 34 may be about 0.070 inches, the height of the barrier wall 24 (e.g., barrier blocks 28) may be about 0.430 inches, and the height of the sidewalls 18 may be about 1.25 inches. The dimensions provided above may be adjusted to accommodate different applications. Generally, however, the height of the ridges 34 should be adequate to decrease the risk of damage to cells caused by turbulence and other disturbances when medium is added to and/or removed from the culture dish 12. In this regard, the channel 32 effectively channels the culture medium to reduce any such fluid disturbances. The height of the ridges 34 should also be adequate to provide a baffling function that effectively dampens any such disturbances (e.g., sloshing) during, for example, manipulation and movement of the culture dish 12. The height of the barrier wall 24 for marking the boundaries of the compartments 22a-22d should be adequate to prevent the biologics from moving over the top of the barrier wall 24, such as, for example, during manipulation and movement of the culture dish 12. Those of ordinary skill in the art will recognize how to vary the dimensions of the culture dish 12, the ridges 34, the barrier wall 24, and/or other aspects of the culture dish 12 to achieve such results.

The bottom wall 16 of culture dish 12 should posses sufficient strength to hold the combined weight of the culture medium and one or more biologics without bending, warping, or otherwise excessively flexing, for example, about 250 grams or more in a 8.75-inch square dish with a depth of about 1.250 inches, as shown in FIGS. 1 and 2. Factors for determining the strength of the bottom wall 16 include the type and thickness of the material(s) used to form the bottom wall 16 of the culture dish 12. For example, when using polystyrene, a standard plastic for forming cell culture dishes, a bottom wall thickness of about 0.750 inches may provide sufficient strength to serve as the bottom wall 16 of an 8.75×8.75 inch culture dish 12. Those of ordinary skill in the art will recognize how to select suitable materials and/or thicknesses to provide sufficient strength and rigidity to bottom wall 16.

Figure 5:
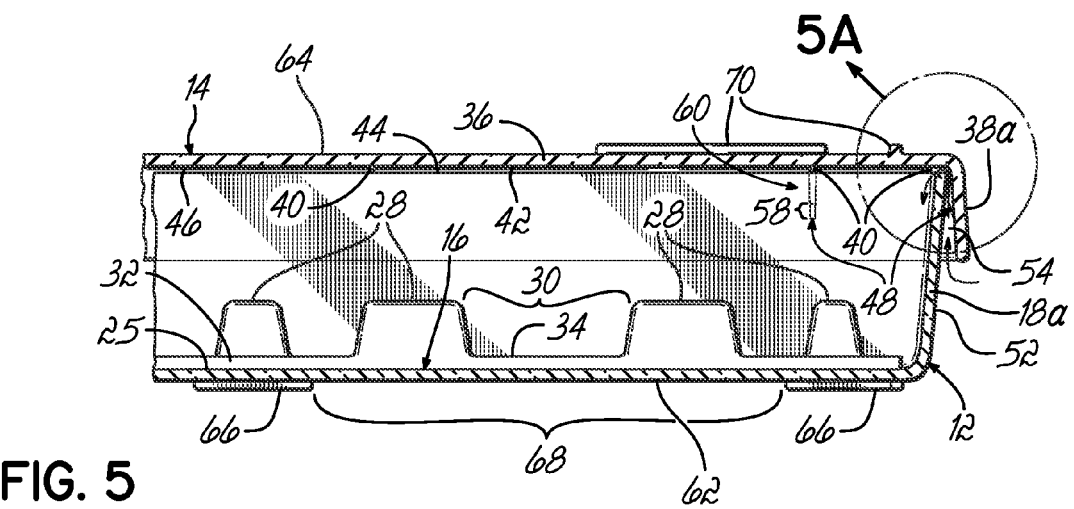
FIG. 5 is a partial cross-sectional view of the culture dish assembly taken generally along line 5-5 in FIG. 4.

In one embodiment, the culture dish assembly 10 further includes a lid 14 adapted to be used with culture dish 12 to minimize contamination and evaporation while also providing air/gas exchange to maintain, for example, the pH of the culture medium or liquid reagents contained in the culture dish 12. As shown in FIGS. 1, 4 and 5, the lid 14 may include a substantially flat top wall 36 and one or more sidewall 38 projecting downwardly from an edge thereof. The lid 14 is sized and shaped to fit over the upper end of the culture dish 12. In one embodiment, it fits with a substantially close fit, as is standard in the industry for bioassay dishes. Thus, in one embodiment, the lid 14 may be generally square having sidewalls 38a-38d that in combination with top wall 36 form lid 14. As noted above with respect to the shape of culture dish 12, other shapes are also possible, the shape of the lid 14 generally corresponding to the shape of the culture dish 12.

Figure 5A:
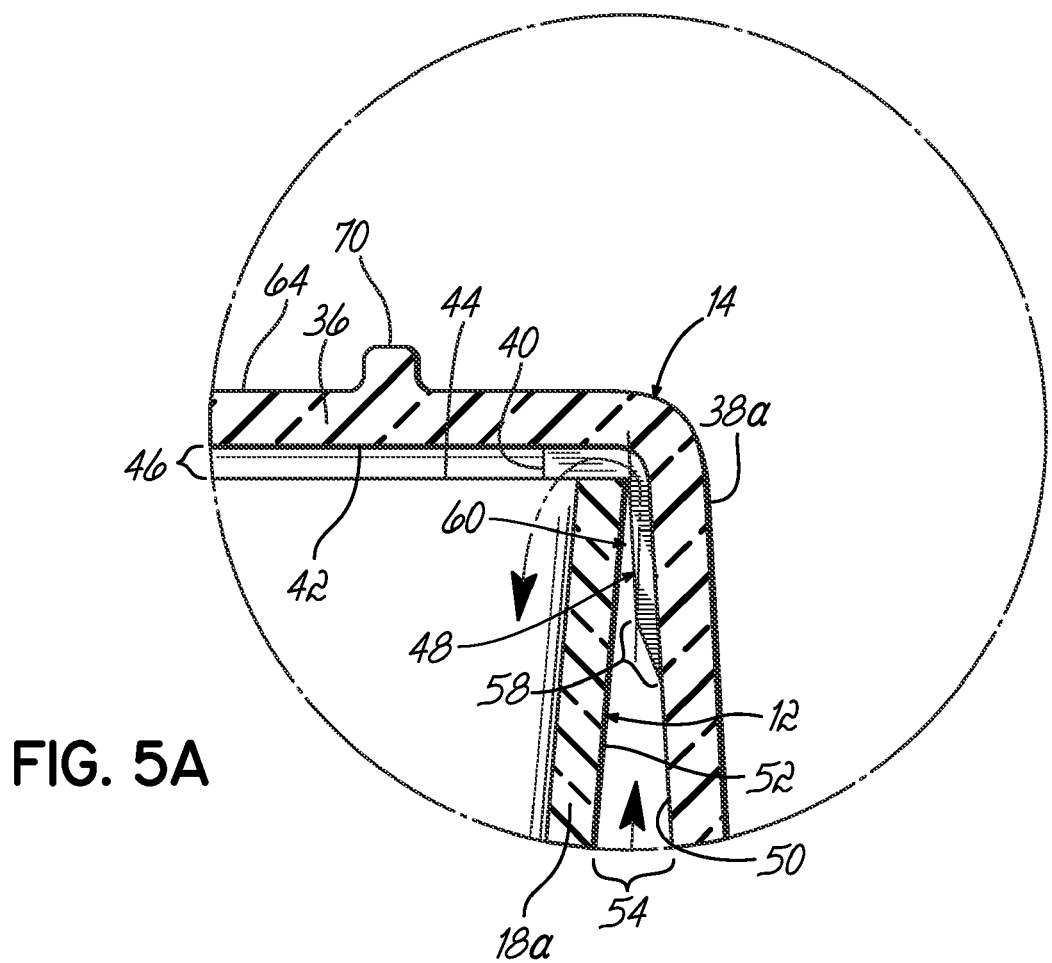
FIG. 5A is an enlarged view of the circled portion of FIG. 5.

As shown in FIGS. 5 and 5A, to facilitate gas exchange with the interior cavity 20 of culture dish 12, the lid 14 may include a plurality of projections, such as vent lugs 40 projecting from the inside surface 42 of the top wall 36 (FIG. 5A). The vent lugs 40 are positioned adjacent the sidewalls 38 so that when the lid 14 is placed on the culture dish 12, the vent lugs 40 engage an upper edge 44 of the sidewalls 18. In this way, the inside surface 42 of the top wall 36 of lid 14 is spaced from the upper edge 44 of the sidewalls 18 to define a plurality of vents or gaps 46 between adjacent vent lugs 40 that permit fluid communication between or about the lugs 40.

Additionally, the lid 14 may include a plurality of projections, such as spacing ribs 48 projecting from the inside surface 50 of the lid sidewalls 38. The spacing ribs 48 are adapted to facilitate uniform or balanced gas exchange by maintaining even spacing between the culture dish 12 and the lid 14 around substantially the entire periphery. When the lid 14 is engaged with the culture dish 12, the spacing ribs 48 may engage an outside surface 52 of the sidewalls 18. Alternatively, the lid 14 may be sized so that there is a slight play between the lid 14 and the culture dish 12 when engaged thereto. In both embodiments, the sidewalls 38 of the lid 14 are spaced from the sidewalls 18 of the culture dish 12 to define a plurality of vents or gaps 54 between adjacent spacing ribs 48. Collectively, the gaps 54 and 46 define a fluid flow path from the outside of the culture assembly 10 to the interior cavity 20 of the culture dish 12, as illustrated in FIG. 5A.

While the embodiment above is shown and described with the vent lugs 40 disposed on the lid 14, the vent lugs 40 may alternatively be disposed along the upper edge 44 of the sidewalls 18, or at other locations that result in a spacing between the top wall 36 of the lid 14 and the upper edge 44 of the culture dish sidewalls 18. In a similar manner, while the spacing ribs 48 are shown and described as being disposed on the inside surface 50 of sidewalls 38 of lid 14, alternatively, the spacing ribs 48 may be disposed on the outside surface 52 of the sidewalls 18 of culture dish 12, or at other locations that result in a space between the sidewalls 18 of the culture dish 12 and the sidewalls 38 of the lid 14. When the spacing ribs 48 are disposed on the lid 14, for example, the ribs 48 may include a tapered end 58 to facilitate aligning the lid 14 with the culture dish 12 when placing the lid 14 thereon. In one embodiment, the vent lugs 40 may be aligned with a corresponding spacing rib 48 to generally define an L-shaped member 60 projecting from the inside surface (top wall and sidewall) of the lid 14.

Figure 6:
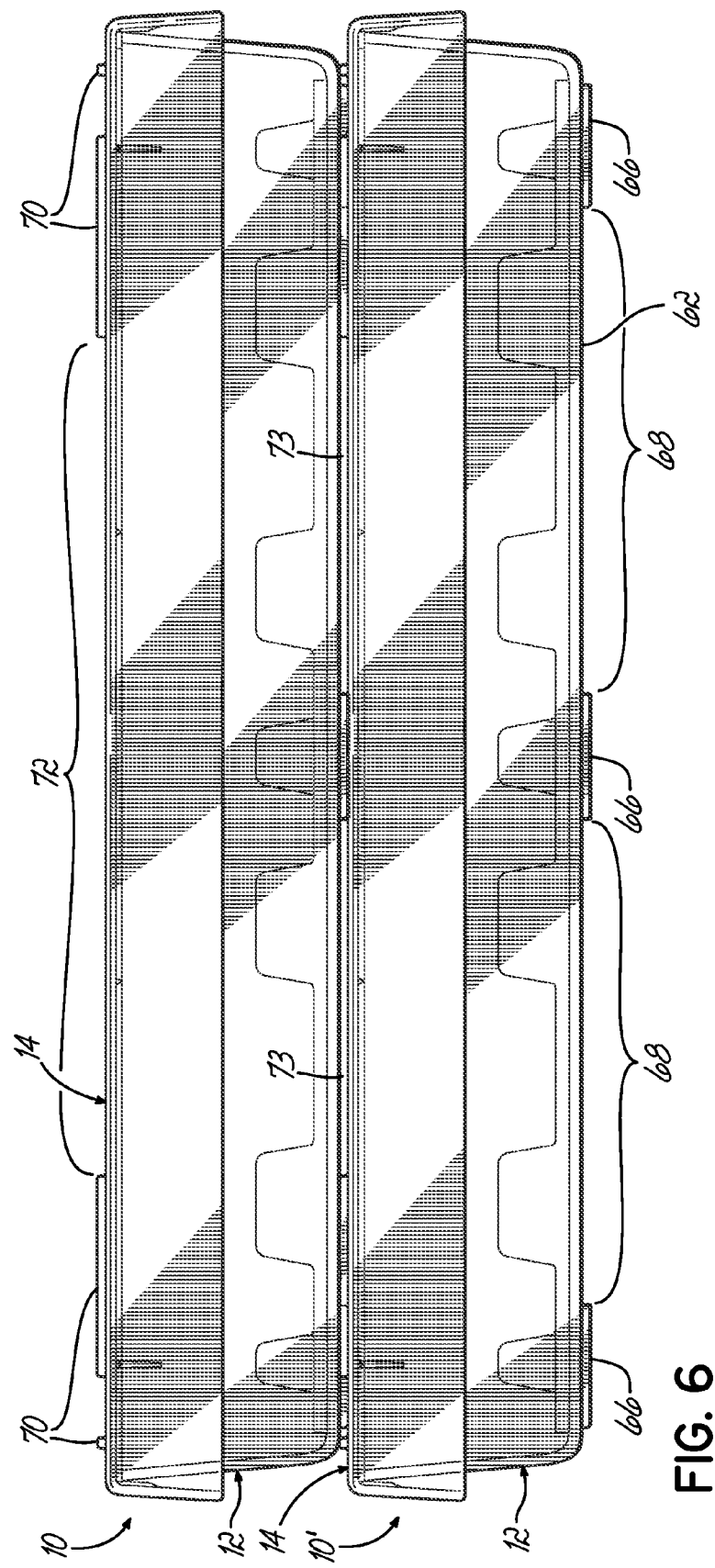
FIG. 6 is a side elevational view of multiple culture dish assemblies in a stacked configuration.

The culture dish assembly 10 may include additional features in accordance with alternate embodiments. For example, the culture dish assembly 10 may include stacking features that permit multiple dish assemblies to be arranged in a stacked configuration. For example, in one embodiment, two to about ten or more culture dish assemblies may be stacked in a stable manner. In this regard, the outside surface 62 of the bottom wall 16 may include a first stacking feature and the outside surface 64 of the top wall 36 may include a second stacking feature that cooperate to prevent or limit lateral movement (e.g., sliding) of one culture dish assembly 10 relative to an adjacent culture dish assembly 10' when in a stacked configuration (FIG. 6). For example, in one embodiment, the outside surface 62 of the bottom wall 16 may include a plurality of projections, such as ridges 66 adjacent one or more of the edges thereof to define a gap 68 between adjacent ridges 66. In one embodiment, at least one ridge 66 is located on each side of the bottom wall 16.

In this embodiment, the outside surface 64 of the top wall 36 may also include a plurality of projections, such as ridges 70 adjacent one or more of the edges thereof to define a gap 72 between adjacent ridges 70. In one embodiment, at least one ridge 70 is located on each side of the top wall 36. The ridges 66 on the bottom wall 16 are configured to nest relative to the ridges 70 on the top wall 36 when two or more (two shown) culture dish assemblies 10, 10' are stacked. For example, the ridges 66 on the bottom wall 16 of the culture dish 12 may be disposed adjacent but interior to the ridges 70 on the top wall 36 of the lid 14. Alternatively, the ridges 66 on the bottom wall 16 may be disposed adjacent but exterior to the ridges 70 on the top wall 36. In both embodiments, the nesting of the ridges 66, 70, prevents or limits the lateral movement (such as by sliding) of one culture dish assembly 10 relative to its adjacent culture dish assembly 10'.

In addition to preventing or limiting movement of adjacent culture dish assemblies 10, 10', for example, the ridges 66, 70 may provide an effective gap 73 and fluid flow path between adjacent culture dish assemblies 10, 10' as shown in FIG. 6.

Such a gap 73 between adjacent culture dish assemblies allows for more uniform gas and temperature exchange between the biologics in the culture dish(es) 12 and the ambient environment. Additionally, the ridges 66 on the outside surface 62 of bottom wall 16 result in an effective non-planar contacting surface. Thus, when the culture dish 12 is placed on a wet support surface (e.g., table, bench, counter, etc.), which may not be uncommon in a laboratory environment, the non-planar aspect of the contacting surface may prevent or reduce the likelihood of the need to apply excessive, jerky forces to the culture dish 12 to dislodge the culture dish 12 from the surface (for example, due to surface tension effects). Such forces typically result in undesired movement (e.g., sloshing, splashing, etc.) of the culture dish contents.

In one embodiment, the culture dish assembly 10 has an orientation indicator for indicating a preferred orientation of the lid 14 relative to the culture dish 12. In some applications, the lid 14 may be removed or otherwise separated from the culture dish 12 one or more times during use. For example, when culture medium is removed and/or added to the culture dish 12, the lid 14 is typically removed from the culture dish 12 and then subsequently placed back on the culture dish 12. In such applications, it may be desirable to locate the lid 14 relative to the culture dish 12 in the same orientation before and after removal. To this end, the culture dish 12 may include a first orientation indicia and the lid 14 may include a second orientation indicia such that when the first orientation indicia is located relative to the second orientation indicia, the lid 14 may be placed on the culture dish 12 in a fixed, pre-determined orientation. By way of example, in one embodiment as shown in FIGS. 1 and 4, the culture dish 12 may include two relatively closely spaced ribs 76 and the lid 14 may include two corresponding relatively closely spaced ribs 78 such that the ribs 76, 78 may be aligned to orient the lid 14 relative to the culture dish 12 (FIG. 1). In one embodiment, the two ribs 76 may be formed in a sidewall 18 of the culture dish 12 and the two ribs 78 may be formed in the outside surface 64 of the top wall 36. Aligning the ribs 78 with the ribs 76 ensures that the lid 14 may be returned to its corresponding culture dish 12 in its original position for every removal thereof.

It should be recognized that the indicia on the culture dish 12 may be positioned at other locations on culture dish 12. Likewise, the indicia on the lid 14 may be positioned at other locations on the lid 14. The locations, however, should be selected so as to be readily visible to facilitate orienting lid 14 relative to the culture dish 12. It should further be recognized that the indicia on the culture dish 12 and lid 14 may include one or more letters, number, symbols, and/or combinations thereof (thus the use of (multiple) ribs 76, 78 above is exemplary and not limiting). In one embodiment, the culture dish assembly 10 may include multiple matching indicia. For example, in addition to ribs 76, 78, the culture dish 12 may include a single rib 80 that is spaced relative to (e.g., aligned with) a single rib 82 on the lid 14 to provide a further indication of the orientation therebetween.

In one embodiment, the culture dish assembly 10 has an indicia 84 for identifying the compartments 22a-22d within the culture dish 12 (FIGS. 1 and 2). In one embodiment, the indicia 84 may be located on the inside surface 25 of the bottom wall 16 and may include one or more letters, number, symbols, and/or combinations thereof. For example, as illustrated in FIG. 2, the compartments 22a-22d may be identified with indicia A, B, C, D. It should be recognized that the other indicia are possible and that the indicia may be positioned at other locations that allow a user to identify a particular compartment.

The described culture dish 12 and lid 14 may be manufactured by various molding processes, such as injection molding processes, as is generally known in the art. Suitable materials for the culture dish 12 include, but are not limited to, polystyrene, styrene-acrylonitrile (SAN), styrene-maleic anhydride (SMA), cyclic olefin copolymers (COC), polycarbonate, acrylic, acrylic-polyvinyl chloride alloys, polypropylene, polypropylene copolymers, polysulfone, polymethylpentene, cellulosic, and other materials compatible with cell culture. In one embodiment, the culture dish 12 and lid 14 may be disposable after use, so material cost may be a factor in determining a suitable material. The culture dish 12 and lid 14 need not be made of the same material. The culture dish 12 and lid 14 may be entirely transparent or portions thereof may be translucent or opaque. In one embodiment, for example, at least a major portion of the bottom wall 16 of the culture dish 12 may be transparent.

The barrier wall 24, such as for example the barrier blocks 28, may be molded as solid features or molded to have about the same thickness as the bottom wall 16 of the culture dish 12 in order to provide for more uniform heating/cooling of the dish material, thereby maintaining more uniform temperatures across the culture dish 12. Alternatively, the barrier wall 24 may be molded as solid features and then drilled or otherwise physically or mechanically hollowed out to have about the same thickness as the bottom wall 16 of the culture dish 12. Those of ordinary skill in the art will recognize other processing methods, either during formation of the culture dish 12 or via post processing methods, for providing a relatively uniform thickness to the bottom wall 16 and barrier wall 24.

After the culture dish 12 is formed, it may be further processed to enhance cell attachment and/or growth, as is generally known in the art. For example, atmospheric corona discharge, DC glow discharge, or radio frequency plasma treatment may be used to change the surface properties of the interior surfaces, or specialized coatings may be applied to one or more surfaces or regions, as is generally known in the art. Examples of such treatments or processes include, but are not limited to, those taught in U.S. Pat. No. 4,452,679 to Dunn et al., U.S. Pat. No. 4,919,659 to Horbett et al., U.S. Pat. No. 4,927,676 to Williams et al., U.S. Pat. No. 5,051,312 to Allmer, U.S. Pat. No. 5,308,704 to Suzuki et al., U.S. Pat. No. 5,449,383 to Chatelier et al., and U.S. Pat. No. 6,617,152 to Bryhan et al., all of which are incorporated by reference herein in their entirety. Alternatively, however, culture dish 12 may be provided without further alteration of the inside surface.

The culture dish assembly 10 may be used for cell culture in much the same way as standard bioassay dishes except that culture media and/or other liquid reagents may be pipetted, poured, or otherwise added to or removed from the one or more channels 32 provided in the culture dish 12 as described above. Also, multiple biologics may be cultured within a single culture dish assembly 10, as provided by embodiments with separate compartments (e.g., 22a-22d). Multiple lidded culture dish assemblies (e.g., 10, 10') may be stacked, as shown in FIG. 6, for containment within an incubator, culture chamber or other processing chamber, transport unit, etc.

The above description is not intended to limit the scope of the appended claims. Additional embodiments and modifications will readily appear to those skilled in the art. Accordingly, departures may be made from such details without departing from the spirit and scope of applicant's inventive concept.

What is claimed is:

1. A device for culturing a biologic in a culture medium, the device comprising:
    a culture dish including a bottom wall and at least one sidewall projecting therefrom to define an interior cavity, the bottom wall being generally planar and configured to support the biologic thereon;
    a pair of spaced apart ridges formed side-by-side in the bottom wall and extending in a common direction to define an elongated channel therebetween, with each of the pair of ridges projecting upwardly from the bottom wall along a respective entire length thereof and having a height that is sufficient to baffle the motion of the culture medium so as to reduce fluid disturbances of the biologic during use;
    a first compartment located on one side of the pair of ridges;
    a second compartment located on the other side of the pair of ridges; and
    at least one barrier wall within at least one of the first or second compartments for partitioning the at least one of the first or second compartments into first and second interior spaces for receiving at least one of a first and a second biologic respectively therein, the at least one barrier wall having a height configured to maintain the first biologic in the first interior space separate from the second biologic in the second interior space,
    wherein the height of the ridges is less than the height of the at least one barrier wall.

2. The device of claim 1, wherein the at least one barrier wall includes at least one opening for providing fluid communication between the first interior space and the second interior space.

3. The device of claim 1, wherein the at least one barrier wall includes a plurality of discrete barrier blocks including a gap between adjacent blocks to provide fluid communication.

4. The device of claim 1, further comprising:
    a lid adapted to be removably coupled to the culture dish to at least partially cover the interior cavity, the lid including a top wall and at least one sidewall projecting therefrom.

5. The device of claim 4, further comprising:
    a least one spacer on one of the culture dish or the lid for providing at least a portion of a fluid flow path from outside the device to the interior cavity of the culture dish.

6. The device of claim 4, further comprising:
    a first projection on the culture dish and a second projection on the lid such that when multiple devices are in a stacked configuration, the first projection on one device cooperates with the second projection on an adjacent device to limit movement of the one device relative to the adjacent device.

7. The device of claim 4, further comprising a first orientation indicator for indicating a specified orientation of the lid relative to the culture dish.

8. The device of claim 7, wherein the first orientation indicator further comprises:
    a first orientation indicia on one of the culture dish or the lid; and
    a second orientation indicia on the other of the culture dish or the lid,
    wherein aligning the first orientation indicia with the second orientation indicia provides the specified orientation of the lid relative to the culture dish.

9. The device of claim 7, wherein the orientation indicator includes at least one of a number, letter, symbol, or combinations thereof.

10. The device of claim 1, further comprising a plurality of indicia for identifying a respective interior space in the culture dish.

11. The device of claim 1, wherein the elongated channel extends across substantially the entire dimension of the bottom wall.

12. The device of claim 1, comprising a plurality of pairs of spaced apart ridges defining multiple channels formed in the bottom wall.

13. The device of claim 1, wherein the culture dish has a width of about 8.75 inches and a length of about 8.75 inches.

14. The device of claim 13, wherein the culture dish has a height of about 1.25 inches.

15. The device of claim 13, wherein the at least one barrier wall has a height of about 0.43 inches.

16. The device of claim 13, wherein each of the pair of ridges have a height of about 0.07 inches.

* * * * *

UNITED STATES PATENT AND TRADEMARK OFFICE
CERTIFICATE OF CORRECTION

| | | |
|---|---|---|
| PATENT NO. | : 8,053,230 B2 | Page 1 of 1 |
| APPLICATION NO. | : 11/846193 | |
| DATED | : November 8, 2011 | |
| INVENTOR(S) | : Keith Owen Whittlinger | |

It is certified that error appears in the above-identified patent and that said Letters Patent is hereby corrected as shown below:

In column 1, line 32, change "Walkersville Md.)," to --Walkersville, Md.),--.

In column 1, line 56, change "Acton Mass.)." to --Acton, Mass.).--.

In column 3, line 47, change "or otherwise effect the culturing" to --or otherwise affect the culturing--.

In column 4, line 65, change "about 0.070 inches," to --about 0.070 inch,--.

In column 4, line 66, change "about 0.430 inches," to --about 0.430 inch,--.

In column 5, line 29, change "about 0.750 inches" to --about 0.750 inch---.

In column 7, line 61, change "may include one or more letters, number, symbols, and/or combinations" to --may include one or more letters, numbers, symbols, and/or combinations--.

In claim 5, column 10, line 2, change "a least one spacer" to --at least one spacer--.

In claim 15, column 10, line 40, change "about 0.43 inches." to --about 0.43 inch.--.

In claim 16, column 10, line 42, change "each of the pair of ridges have" to --each of the pair of ridges has--.

In claim 16, column 10, line 42, change "about 0.07 inches." to --about 0.07 inch.--.

Signed and Sealed this
Third Day of January, 2012

David J. Kappos
*Director of the United States Patent and Trademark Office*